United States Patent
Friedlander et al.

(10) Patent No.: US 8,990,033 B2
(45) Date of Patent: Mar. 24, 2015

(54) MONITORING OPERATIONAL CONDITIONS OF A CARGO SHIP THROUGH USE OF SENSOR GRID ON INTERMODAL CONTAINERS

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 549 days.

(21) Appl. No.: 13/192,149

(22) Filed: Jul. 27, 2011

(65) Prior Publication Data

US 2013/0030725 A1 Jan. 31, 2013

(51) Int. Cl.
| | | |
|---|---|---|
| *G01H 1/12* | (2006.01) | |
| *G01H 1/14* | (2006.01) | |
| *G01H 1/16* | (2006.01) | |
| *G01R 23/16* | (2006.01) | |
| *G01R 23/18* | (2006.01) | |
| *G08B 13/16* | (2006.01) | |
| *G08B 29/04* | (2006.01) | |
| *B63B 17/00* | (2006.01) | |

(52) U.S. Cl.
CPC ............... *G01H 1/12* (2013.01); *G08B 29/04* (2013.01); *B63B 2017/0009* (2013.01)
USPC .................. 702/56; 702/54; 702/71; 702/76; 702/77; 340/539.12; 340/566

(58) Field of Classification Search
USPC ........ 702/56, 54, 71, 76, 77; 340/539.22, 566
See application file for complete search history.

(56) References Cited

U.S. PATENT DOCUMENTS

| 3,820,381 A | 6/1974 | Thurston |
| 3,838,421 A | 9/1974 | Dasse-Hartaut et al. |
| 4,073,183 A | 2/1978 | Byalko et al. |

(Continued)

FOREIGN PATENT DOCUMENTS

| JP | 52104960 A | 9/1977 |
| JP | 4235380 A | 8/1992 |

(Continued)

OTHER PUBLICATIONS

U.S. Appl. No. 13/192,887—Non-Final Office Action Mailed Feb. 7, 2013.

(Continued)

*Primary Examiner* — Andrew Schechter
*Assistant Examiner* — Alexander Satanovsky
(74) *Attorney, Agent, or Firm* — John R. Pivnichny; Law Office of Jim Boice

(57) ABSTRACT

A computer-implemented method, system, and/or computer program product monitors operational conditions of a cargo ship. A baseline composite vibration pattern is established from readings generated by multiple smart sensors. Each of the multiple smart sensors is a uniquely-identified smart sensor that has been affixed to one of multiple intermodal shipping containers that have been loaded onto a cargo ship, and each smart sensor includes a vibration sensor for detecting mechanical vibration. Subsequent readings are then taken from the multiple smart sensors to generate a new composite vibration pattern. In response to the new composite vibration pattern being different from the baseline composite vibration pattern, the new composite vibration pattern is matched with a known composite vibration pattern in order to identify a cause of the new composite vibration pattern.

20 Claims, 5 Drawing Sheets

(56) References Cited

U.S. PATENT DOCUMENTS

| | | | |
|---|---|---|---|
| 4,186,590 A | | 2/1980 | Egorov et al. |
| 4,511,247 A | | 4/1985 | McGovern et al. |
| 4,530,233 A | | 7/1985 | Kadi |
| 5,195,046 A | * | 3/1993 | Gerardi et al. .......... 702/35 |
| 5,549,803 A | | 8/1996 | Schoess et al. |
| 5,681,986 A | | 10/1997 | Merk et al. |
| 5,736,940 A | | 4/1998 | Burgener |
| 6,260,004 B1 | | 7/2001 | Hays et al. |
| 6,265,979 B1 | | 7/2001 | Chen et al. |
| 6,718,270 B2 | | 4/2004 | Horiuchi et al. |
| 6,950,767 B2 | | 9/2005 | Yamashita et al. |
| 7,228,740 B2 | | 6/2007 | Sinha |
| 7,325,759 B2 | * | 2/2008 | Meyer .................. 241/30 |
| 7,343,136 B2 | | 3/2008 | Liu et al. |
| 7,535,355 B2 | * | 5/2009 | Barone ................ 340/566 |
| 7,627,441 B2 | | 12/2009 | Longsdorf et al. |
| 7,630,948 B2 | | 12/2009 | Friedlander et al. |
| 7,693,663 B2 | | 4/2010 | Friedlander et al. |
| 7,720,574 B1 | | 5/2010 | Roys |
| 7,762,142 B2 | | 7/2010 | Rakow et al. |
| 8,154,723 B2 | | 4/2012 | Fu et al. |
| 8,538,667 B2 | | 9/2013 | Friedlander et al. |
| 2004/0122787 A1 | | 6/2004 | Avinash et al. |
| 2005/0011278 A1 | | 1/2005 | Brown et al. |
| 2005/0256885 A1 | | 11/2005 | Yairi et al. |
| 2006/0071786 A1 | * | 4/2006 | Fano ................ 340/539.22 |
| 2006/0097983 A1 | | 5/2006 | Haggman et al. |
| 2006/0285350 A1 | | 12/2006 | Wang |
| 2007/0050121 A1 | | 3/2007 | Ammon et al. |
| 2007/0199382 A1 | | 8/2007 | Sakai |
| 2008/0009099 A1 | | 1/2008 | Kishkovich et al. |
| 2008/0077463 A1 | | 3/2008 | Friedlander et al. |
| 2008/0180281 A1 | | 7/2008 | Bilimoria et al. |
| 2008/0270034 A1 | | 10/2008 | Friedlander et al. |
| 2008/0274553 A1 | | 11/2008 | Bratton et al. |
| 2009/0157302 A1 | | 6/2009 | Tashev et al. |
| 2009/0271100 A1 | | 10/2009 | Kim et al. |
| 2010/0150359 A1 | * | 6/2010 | KnicKrehm et al. ........ 381/58 |
| 2010/0189291 A1 | * | 7/2010 | Aharoni et al. ........... 381/313 |
| 2010/0268469 A1 | | 10/2010 | Harrison et al. |
| 2011/0085156 A1 | | 4/2011 | Jones et al. |
| 2011/0153208 A1 | | 6/2011 | Kruglick |
| 2011/0173067 A1 | | 7/2011 | Herbst et al. |
| 2011/0308638 A1 | | 12/2011 | Hyland et al. |
| 2013/0030613 A1 | | 1/2013 | Friedlander et al. |
| 2013/0030680 A1 | | 1/2013 | Friedlander et al. |
| 2013/0030724 A1 | | 1/2013 | Friedlander et al. |
| 2013/0040399 A1 | | 2/2013 | Belbruno et al. |

FOREIGN PATENT DOCUMENTS

| | | |
|---|---|---|
| JP | 05052972 U | 7/1993 |
| JP | 07044117 A | 2/1995 |
| JP | 08085496 A | 4/1996 |
| JP | 2006194795 A | 7/2006 |
| JP | 2007531868 A | 11/2007 |
| WO | 2008052786 A1 | 5/2008 |
| WO | 2010071607 A1 | 6/2010 |

OTHER PUBLICATIONS

U.S. Appl. No. 13/252,342—Specification Filed Oct. 4, 2011.

U.S. Appl. No. 13/252,342—Non-Final Office Action Mailed Nov. 9, 2012.

R. Marinelli, "FAA Runway Friction Program", Runway Condition Determination, Reporting, and Report Dissemination Workshop, Jun. 20, 2006, pp. 1-13.

T. Yager, "Runway Friction Measurement", FAA/Aviation Industry Workshop on Runway Condition Determination, Reporting, and Report Dissemination, Aug. 7-8, 2006, pp. 1-15.

Douglas Equipment International Inc., Special Products Division "Mu-Meter MK 6-Specification" PDF Retrieved From http://www.douglas-equipment.com/product_display.php?id=0000000035, pp. 1-2.

N. Harrington, "Knock-Based Commands for Your Linux Laptop", pp. 1-11, Jul. 25, 2006, http://www.ibm.com/developerworks/library/I-knockage/index.html.

W. Xie et al., "A New Diagnostic Method of Bolt Loosening Detection for Thermal Protection Systems", Proceedings of the SPIE—The International Society for Optical Engineering, vol. 7493, 2009.

S. Lihua et al., "Applications of Piezoelectric Material Sensors in Smart Structures", Transactions of Nanjing University of Aeronautics & Astronautics, vol. 1, No. 2, 210-213, Dec. 1996.

J. Schoess et al., "Smart Aircraft Fastener Evaluation (SAFE) System—A Condition-Based Corrosion Detection System for Aging Aircraft", Proceedings of the SPIE—The International Society for Optical Engineering, vol. 2718, 175-184, 1996.

J. Schoess et al., "Smart Fastener for KC-135 Structural Integrity Monitoring", Proceedings of the SPIE—The International Society for Optical Engineering, vol. 3042, pp. 278-282, 1997.

T. Bojko, "Smart Sensor Solutions for Mechanical Measurements and Diagnostics", Metrology and Measurement Systems, vol. 12, No. 1, 2005, pp. 95-103.

S. Kessler, "Piezoelectric-Based In-Situ Damage Detection of Composite Materials for Structural Health Monitoring Systems", Doctorate of Philosophy in Aeronautics and Astronautics at the Massachusetts Institute of Technology, 2002, pp. 1-200.

D. Sinha, "Acoustic Sensor for Pipeline Monitoring: Technology Report", Los Alamos National Laboratory, Jul. 20, 2005, pp. 1-23.

B. Umeadi et al., "The Development of an Intelligent Sensor for the Monitoring of Pipeline System Integrity", Oil and Gas 2008, pp. 1-4.

C. Zang et al., "Structural Health Monitoring and Damage Assessment Using Frequency Response Correlation Criteria", Journal of Engineering Mechanics, Sep. 2007, 981-993.

S.L. Hung et al., "Aiming for the Top University Plan: Preliminary Results" 2009, http://www.cv.nctu.edu.tw/~wwwadm/chinese/monitoring2/result.html.

U.S. Appl. No. 11/741,186, filed Apr. 27, 2007, Friedlander, et al.: Prosecution History.

United Kingdom Patent Application No. GB1216790.4, Combined Search and Examination Report, Jan. 18, 2013, pp. 1-5.

International Searching Authority, International Search Report and Written Opinion, Dec. 18, 2012, pp. 1-6.

U.S. Appl. No. 13/962,665—Non-Final Office Action Mailed Sep. 27, 2013.

U.S. Appl. No. 13/190,172—Non-Final Office Action Mailed Sep. 25, 2013.

U.S. Appl. No. 13/962,665—Notice of Allowance Mailed Jan. 3, 2014.

UK IPO, GB Patent Application No. 1401834.5—Examination Report Mailed Mar. 18, 2014.

* cited by examiner

US 8,990,033 B2

MONITORING OPERATIONAL CONDITIONS OF A CARGO SHIP THROUGH USE OF SENSOR GRID ON INTERMODAL CONTAINERS

BACKGROUND

The present disclosure relates to the field of electronics, and specifically to electronic devices used in sensor arrays. Still more particularly, the present disclosure relates to sensor arrays used to monitor operational conditions of a cargo ship.

Vibration detection devices are used to detect and transpose mechanical vibration energy into analogous electrical signals that represent the detected mechanical vibration energy. A vibration detection device uses a motion sensitive component, such as an accelerometer, a piezoelectric device (e.g., a tuned crystal), etc. to make these mechanical-to-electrical transformations.

SUMMARY

A computer-implemented method, system, and/or computer program product monitors operational conditions of a cargo ship. A baseline composite vibration pattern is established from readings generated by multiple smart sensors. Each of the multiple smart sensors is a uniquely-identified smart sensor that has been affixed to one of multiple intermodal shipping containers that have been loaded onto a cargo ship, and each smart sensor includes a vibration sensor for detecting mechanical vibration. Subsequent readings are then taken from the multiple smart sensors to generate a new composite vibration pattern. In response to the new composite vibration pattern being different from the baseline composite vibration pattern, the new composite vibration pattern is matched with a known composite vibration pattern in order to identify a cause of the new composite vibration pattern.

DETAILED DESCRIPTION

Figure 1:
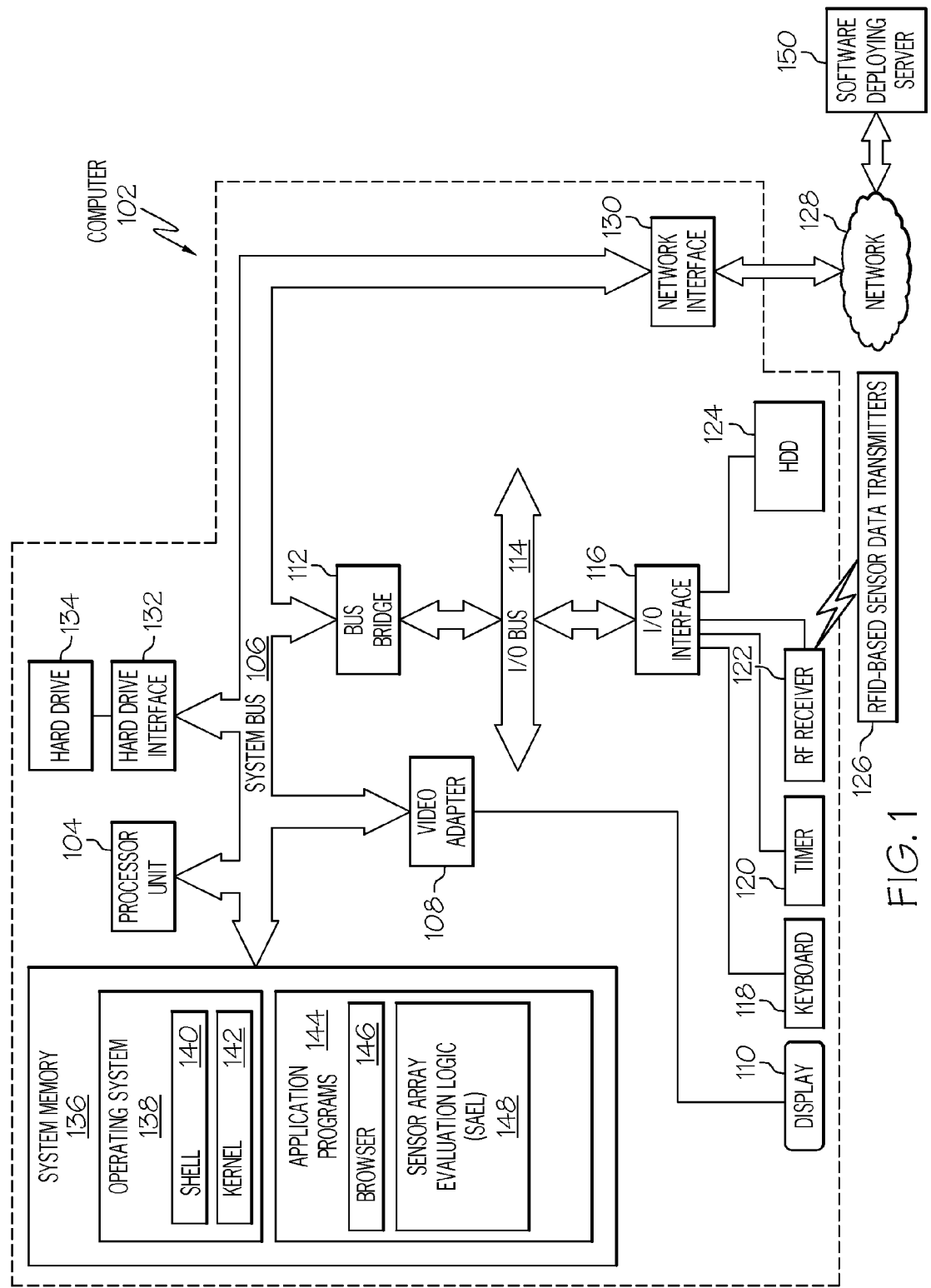
FIG. 1 depicts an exemplary computer in which the present invention may be utilized.

As will be appreciated by one skilled in the art, the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary computer 102, which the present invention may utilize. Note that some or all of the exemplary architecture shown for computer 102 may be utilized by software deploying server 150.

Computer 102 includes a processor unit 104, which may utilize one or more processors each having one or more processor cores, that is coupled to a system bus 106. A video adapter 108, which drives/supports a display 110, is also coupled to system bus 106. System bus 106 is coupled via a bus bridge 112 to an Input/Output (I/O) bus 114. An I/O interface 116 is coupled to I/O bus 114. I/O interface 116 affords communication with various I/O devices, including a keyboard 118, a timer 120, a Radio Frequency (RF) receiver 122, a Hard Disk Drive (HDD) 124, and Radio Frequency Identification (RFID) based sensor data transmitters 126, which communicate wirelessly with the RF receiver 122. Note that, in one embodiment, elements 122 and 126 are hardwired together, such that readings from the sensors (element 126) are able to be transmitted via wiring to a receiver (e.g., element 122). Note also that the format of the ports connected to I/O interface 116 may be any known to those skilled in the art of computer architecture, including but not limited to Universal Serial Bus (USB) ports.

Computer 102 is able to communicate with a software deploying server 150 via a network 128 using a network interface 130, which is coupled to system bus 106. Network 128 may be an external network such as the Internet, or an internal network such as an Ethernet or a Virtual Private Network (VPN).

A hard drive interface 132 is also coupled to system bus 106. Hard drive interface 132 interfaces with a hard drive 134. In a preferred embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a World Wide Web (WWW) client (i.e., computer 102) to send and receive network messages to the Internet using HyperText Transfer Protocol (HTTP) messaging, thus enabling communication with software deploying server 150 and other described computer systems.

Application programs 144 in computer 102's system memory (as well as software deploying server 150's system memory) also include a Sensor Array Evaluation Logic (SAEL) 148. SAEL 148 includes code for implementing the processes described below, and particularly as described in reference to FIGS. 2-8. In one embodiment, computer 102 is able to download SAEL 148 from software deploying server 150, including in an on-demand basis. Note further that, in one embodiment of the present invention, software deploying server 150 performs all of the functions associated with the present invention (including execution of SAEL 148), thus freeing computer 102 from having to use its own internal computing resources to execute SAEL 148.

The hardware elements depicted in computer 102 are not intended to be exhaustive, but rather are representative to highlight essential components required by the present invention. For instance, computer 102 may include alternate memory storage devices such as magnetic cassettes, Digital Versatile Disks (DVDs), Bernoulli cartridges, and the like. These and other variations are intended to be within the spirit and scope of the present invention.

Figure 2:
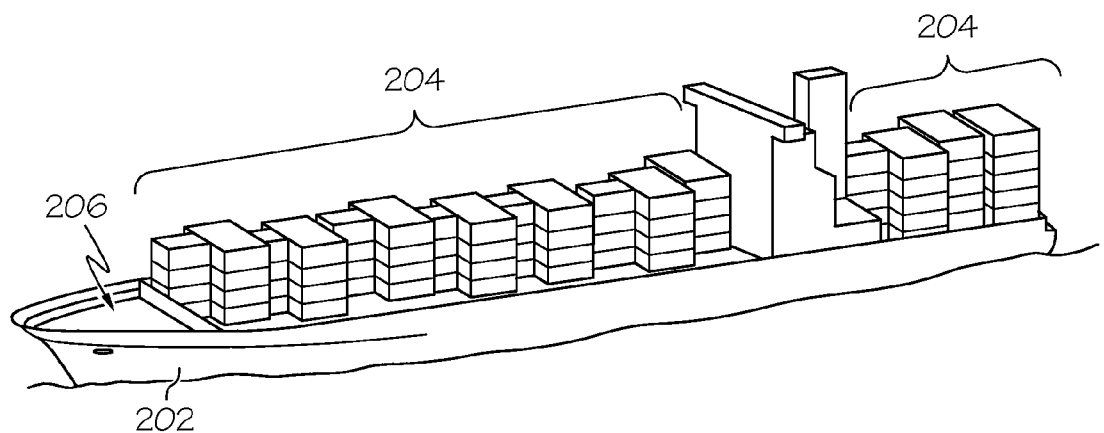
FIG. 2 illustrates an exemplary ship on which are loaded multiple intermodal containers, each of which has an affixed vibration sensor, which optionally is Radio Frequency Identification (RFID) enabled.

With reference now to FIG. 2, an exemplary ship 202 on which the present invention may be utilized is illustrated. The ship 202 is a cargo ship that carries multiple intermodal containers 204 on the deck/hold 206 of the ship. In one embodiment, these intermodal containers 204 are uniform in size and shape, such that they stack next to and on top of one another, and so that they are capable of being transported on land by appropriately configured container trucks.

Figure 3:
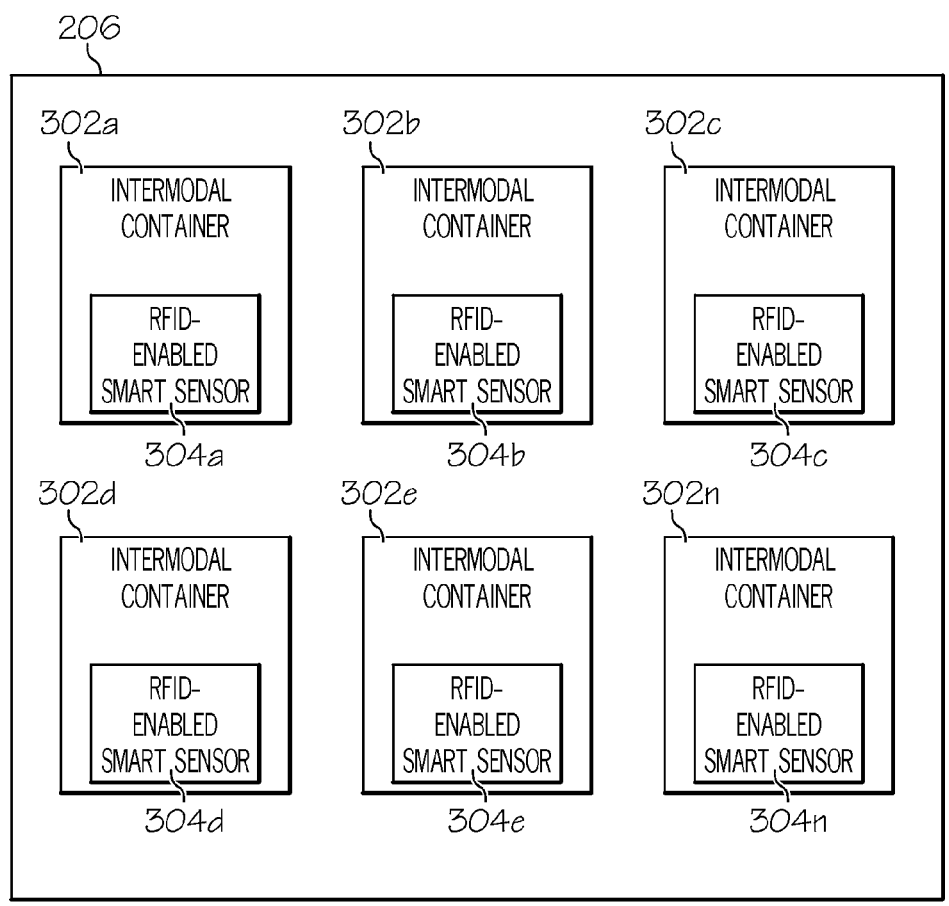
FIG. 3 depicts an exemplary layout of a portion of the multiple intermodal containers shown in FIG. 2.

As illustrated in FIG. 3, a top (or side) view of the multiple intermodal containers 204 positioned on deck/hold 206 in FIG. 2 are depicted as multiple intermodal shipping containers 302a-n (where "n" is an integer). In one embodiment, affixed to each intermodal container is a separate and distinct uniquely-identified RFID-enabled smart sensor from RFID-enabled smart sensors 304a-n. Note that while the smart sensors 304a-n are RFID-enabled in one embodiment, in another embodiment these smart sensors 304a-n do not include an RFID. In this embodiment, the locations of the different smart sensors 304a-n are identified by maps, loading plans, etc. for the multiple intermodal shipping containers 302a-n.

Figure 4:
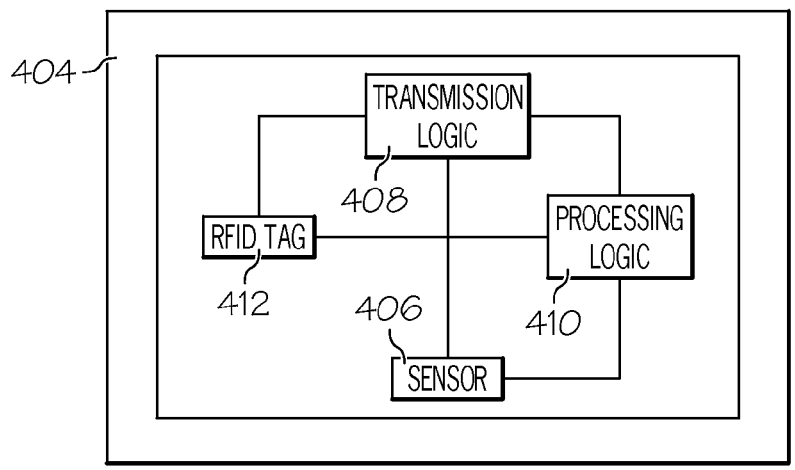
FIG. 4 illustrates an exemplary RFID enabled sensor that is affixed to one of the multiple intermodal containers shown in FIG. 3.

Additional detail of an exemplary RFID-enabled smart sensor is illustrated in FIG. 4 as RFID-enabled smart sensor 406 (which shows additional detail of each of the RFID-enabled smart sensors 304a-n shown in FIG. 3). Within the RFID-enabled smart sensor 406 is a sensor 404. Sensor 404 is able to sense mechanical vibration (i.e., vibrations that are propagated through a solid medium such as metal), acoustic vibration (i.e., vibrations that are propagated through air), chemicals (e.g., low levels of airborne chemicals), radiation (i.e., levels of radioactivity), and/or electromagnetism (i.e., electromagnetism (EM) throughout the EM spectrum, including ultraviolet light, visible light, etc.).

In one embodiment, sensor 404 is directly coupled to a transmission logic 408, which is able to transmit the raw information detected by the sensor 404 to a receiver (e.g., RF receiver 122 shown in FIG. 1). For example, assume that sensor 404 detects mechanical vibrations through the use of an internal crystal-based strain gauge. The sensor 404 transduces these mechanical vibrations into electrical analog signals, which can be directly transmitted by the transmission logic 408. In another embodiment, however, the transduced mechanical vibrations are first sent to a local processing logic 410 within the RFID-enabled smart sensor 406. This processing logic 410 is able to quantify and digitize the transduced mechanical vibrations before they are sent to the transmission logic 408.

Note that in one embodiment, an RFID tag 412 is also a component of the RFID-enabled smart sensor 406. The RFID tag 412, which is different/unique to each RFID-enabled smart sensor 406 (and thus the intermodal shipping container to which it is affixed), stores and communicates Electronic Product Code (EPC) information. The EPC information includes information about the contents of the intermodal shipping container to which the RFID tag is attached; the source/destination of that intermodal shipping container; any safety/hazard information (e.g., Material Safety Data Sheet—MSDS information) about contents of that intermodal shipping container; any product expiration information about the contents of that intermodal shipping container; product lot numbers for the contents of that intermodal shipping container; the name, location, and contact information of the manufacturer of the contents of that intermodal shipping container, etc. The RFID tags may be active (i.e., battery powered), semi-passive (i.e., powered by a battery and a capacitor that is charged by an RF interrogation signal), or purely passive (i.e., either have a capacitor that is charged by an RF interrogation signal or are geometrically shaped to reflect back specific portions of the RF interrogation signal). These passive RFID tags may contain an on-board Integrated Circuit (IC) chip, or they may be chipless.

Figure 5:
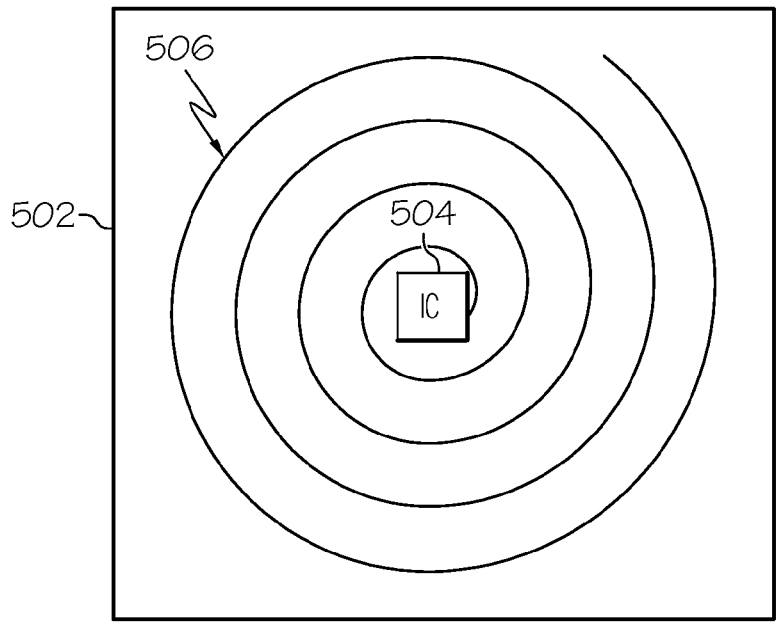
FIG. 5 depicts an exemplary RFID tag that may be used by the present invention.
Figure 6:
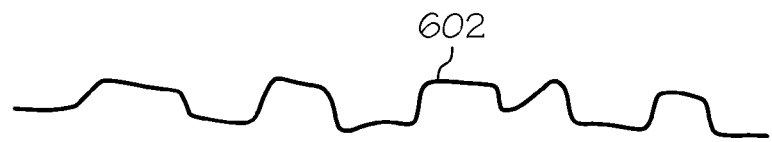
FIG. 6 illustrates an exemplary chipless RFID tag that may be used by the present invention.

With reference now to FIGS. 5-6, exemplary RFID tags are depicted. More specifically, FIG. 5 depicts an exemplary chip-enabled RFID tag 502, which is a passive RFID tag that has an on-board IC chip 504 and a coupled antenna 506. The IC chip 504 stores and processes information, including EPC information that describes information (including name, chemical composition, manufacturer, lot number, etc.) of material stored within the affixed-to intermodal shipping container. The IC chip 504 may contain a low-power source (e.g., a capacitor, not shown, that is charged by an interrogation signal received by the coupled antenna 506). Upon the capacitor being charged, the RFID tag 502 then generates a radio signal, which includes the EPC information stored in the IC chip 504, to be broadcast by the coupled antenna 506.

FIG. 6 illustrates an exemplary chipless RFID tag 602. As the name implies, chipless RFID tag 602 does not have an IC chip, but is only an antenna that is shaped to reflect back a portion of an interrogation signal. That is, the chipless RFID tag 602 (also known as a Radio Frequency (RF) fiber) is physically shaped to reflect back select portions of a radio interrogation signal from an RF transmission source. Chipless RFID tag 602 typically has a much shorter range than that of chip-enabled RFID tag 502. Furthermore, the amount of information that chipless RFID tag 602 can return is much smaller than that of chip-enabled RFID tag 502, which is able to store relatively large amounts of data in the on-board IC chip 504.

Figure 7:
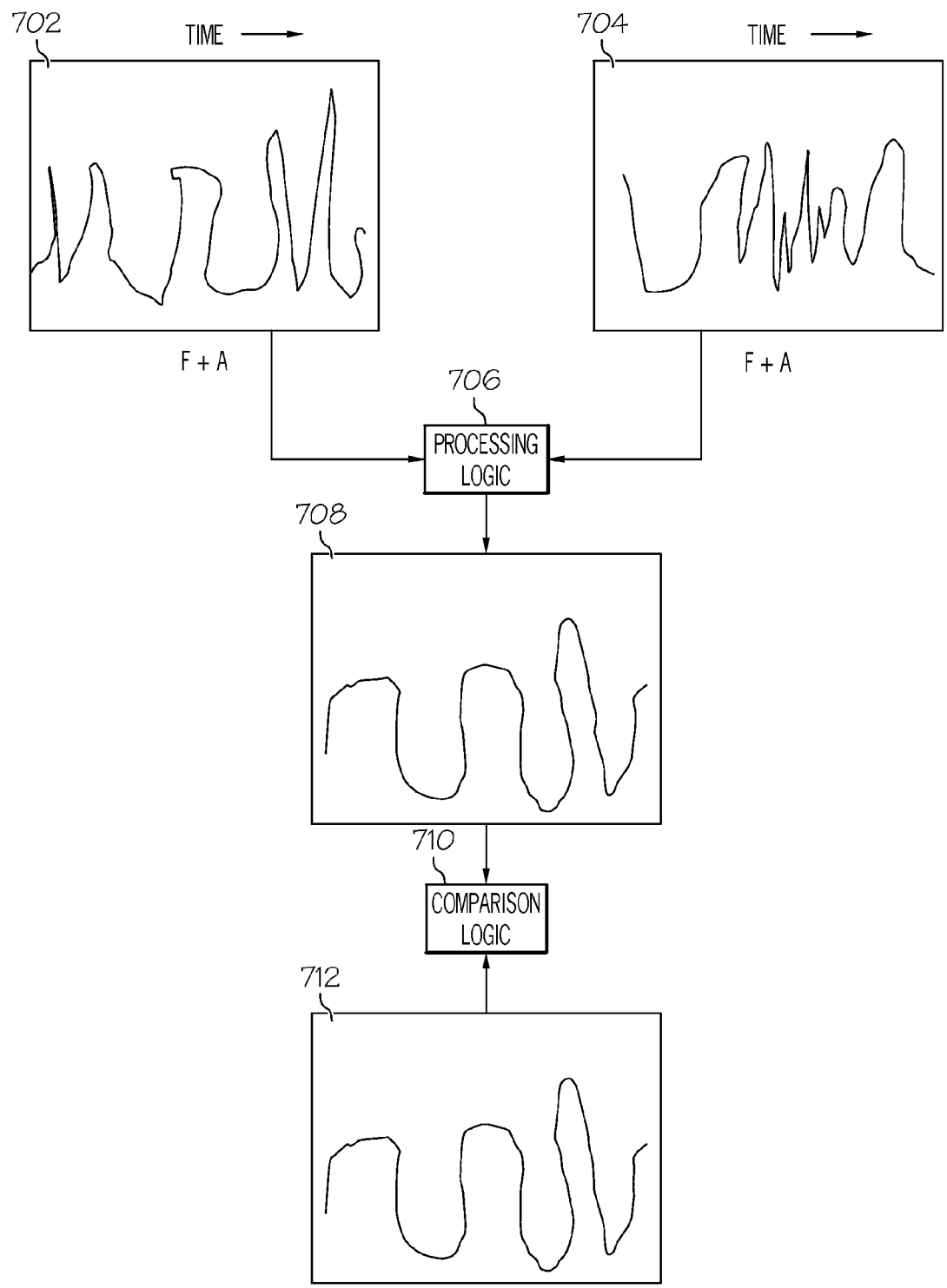
FIG. 7 depicts an exemplary combination of frequency (F) plus amplitude (A) vibration patterns, from uniquely-identified smart sensors on different intermodal containers, being processed to create a new composite vibration pattern, which is then compared to a known vibration pattern in order to identify a cause for a change in the new composite vibration pattern from a baseline composite vibration pattern.

With reference now to FIG. 7, signals 702 and 704 are generated by two distinct and physically separate (possibly RFID-enabled) smart sensors (e.g., RFID-enabled smart sensor 304a and RFID-enabled smart sensor 304e shown in FIG. 3). For example, assume that RFID-enabled smart sensors 304a and 304e both have internal mechanical vibration sensors (e.g., element 406 shown in FIG. 4). The RFID-enabled smart sensor 304a detects and transduces mechanical vibration to generate a frequency (F) and amplitude (A) vibration pattern 702, while the RFID-enabled smart sensor 304e detects and transduces other mechanical vibrations to generate another F+A vibration pattern 704. These two F+A vibration patterns 702 and 704 are then sent to a processing logic 706 (e.g., computer 102 shown in FIG. 1), either as raw analog signals or as processed (e.g., by processing logic 410 shown in FIG. 4) signals via a transmission logic (e.g., transmission logic 408 shown in FIG. 4). The processing logic 706 generates, by combining the two F+A vibration patterns 702 and 704, a composite vibration pattern 708. As will be discussed below, the composite vibration pattern 708 may be a "baseline" pattern. This "baseline" pattern may be a pattern that is arbitrarily generated at some point in time during a voyage of the cargo ship, or it may be generated at a time that other information sensors/analysis indicates that the operational conditions (i.e., positioning of the multiple intermodal shipping containers, operational condition of the cargo ship's drive train, structural integrity of the cargo ship, etc.) are all within predefined acceptable ranges (i.e., the cargo ship is running properly according to predefined parameters for load arrangements, structural integrity, condition of the engine/propeller/etc.).

Assume now for explanatory purposes that the composite vibration pattern 708 is not a baseline composite vibration pattern, but rather is a new composite vibration pattern that has been generated by taking subsequent readings (e.g., after taking readings to create the baseline composite vibration pattern) from the RFID-enabled smart sensor 304a and RFID-enabled smart sensor 304e shown in FIG. 3. In this scenario, a comparison logic 710 receives a copy of the new composite vibration pattern 708, which is sent from the processing logic 706. Comparison logic 710 may be part of a same computing system (e.g., computer 102 shown in FIG. 1) as the processing logic 706, or the comparison logic 710 may be remote from the processing logic 706, such that the new composite vibration pattern 708 is transmitted over a network (wireless or wired) from the processing logic 706 to the comparison logic 710.

Once the comparison logic 710 has a copy of the new composite vibration pattern 708, it compares the new composite vibration pattern 708 to a known composite vibration pattern 712. The known composite vibration pattern 712, which may be stored locally within the comparison logic 710, or may be stored remotely at a remote storage device, cloud, etc., is associated with (e.g., using a lookup table or other database) a particular cause. That is, historical, empirical, and/or simulated observations reveal that if a pattern has a same waveform as the known composite vibration pattern 712, then a conclusion is reached that whatever previously caused the known composite vibration pattern 712 (whether by actual conditions or through simulation) is now causing the same new composite vibration pattern 708. Note that the new composite vibration pattern 708 is generated by combining vibration patterns from similar sensors (e.g., the type, age, and condition of the sensor in the RFID-enabled smart sensor) in similar locations (i.e., affixed to similar type of intermodal shipping container at a same location in the stack of intermodal shipping containers and at a similar physical location on the cargo ship) under similar conditions (e.g., during similar sea and weather conditions, similar ship speed, etc.) as those that generated the known composite vibration pattern 712. The event/cause that resulted in the new/known composite vibration patterns 708/712 may be a shift (e.g., inadvertent movement) of one or more of the intermodal containers (which may or may not be the intermodal containers that have affixed thereon the RFID-enabled smart sensors that generated the vibration patterns); a change in the physical integrity of the cargo ship (e.g., a broken or loose piece of hull, a cracked/broken support structure, etc.); a change to the ship's drive train (e.g., a crack/break in a propeller/screw, a damaged/broken bearing/shaft/rod/piston in the engine, etc.), or any other predefined/predescribed operational condition of the cargo ship.

Figure 8:
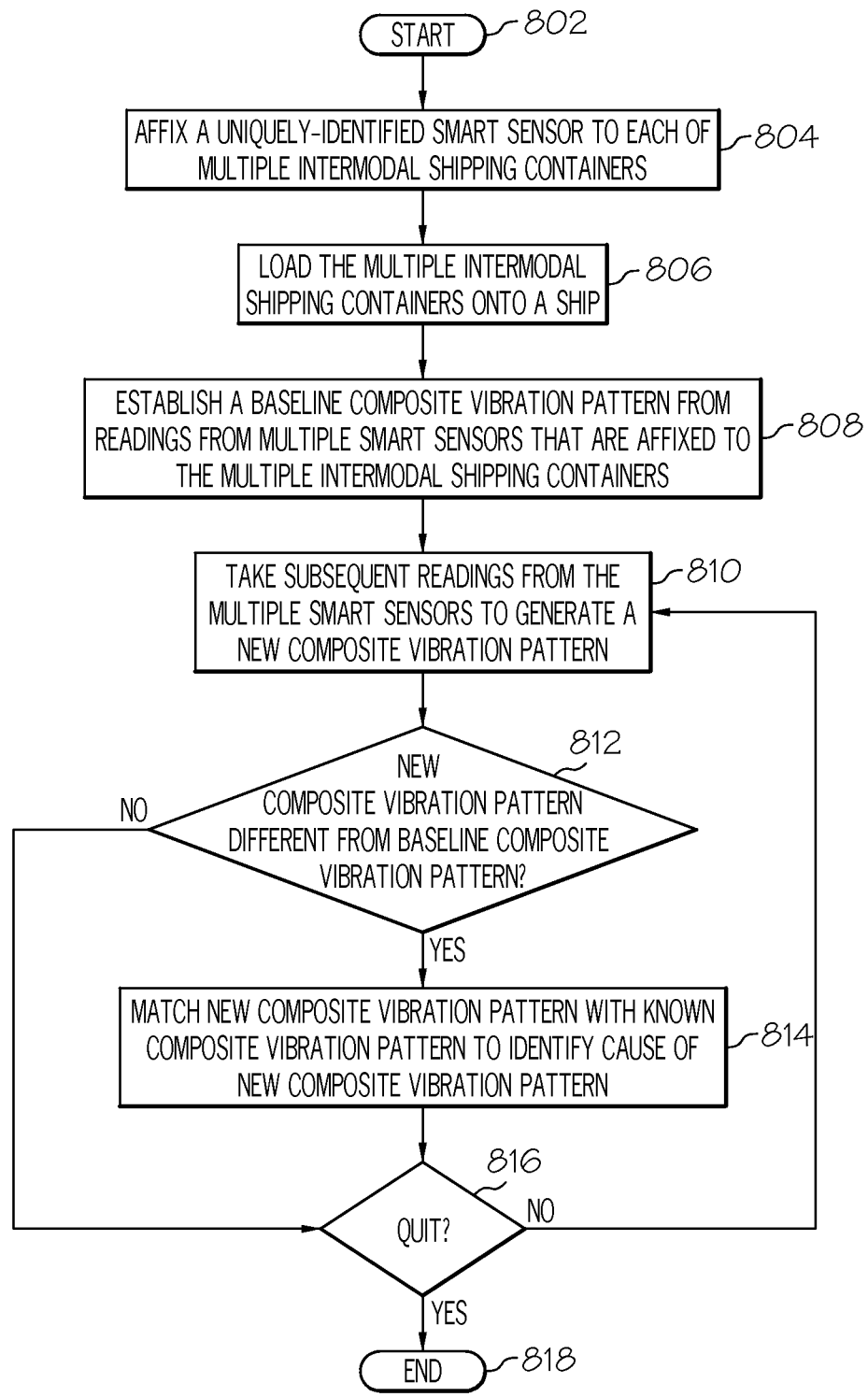
FIG. 8 is a high-level flow chart of one or more exemplary steps performed by a processor to monitor operational conditions of a cargo ship in accordance with one embodiment of the present invention.

Referring now to FIG. 8, a high-level flow chart of one or more exemplary steps performed by a processor to monitor operational conditions of a cargo ship in accordance with one embodiment of the present invention is presented. After initiator block 802, a uniquely-identified smart sensor is affixed to one or more of multiple intermodal shipping containers (block 804). Each uniquely-identified smart sensor identifies the intermodal shipping container to which it is attached, as well as the location of where that particular intermodal shipping container is positioned on the cargo ship. As described in block 806, the multiple intermodal shipping containers (some or all of which have affixed thereon a uniquely-identified smart sensor, which may be RFID-enabled as described above) are loaded onto the cargo ship. The loading order and/or information from the smart sensors tells a computer, which may be on the cargo ship or may be at a remote location, where the various smart sensors are located, as well as the environment in which they are situated. This environmental information includes, but is not limited to, how the respective intermodal shipping containers are stacked/positioned/etc.; what type of intermodal shipping container (i.e., its size, weight composition, content, etc.) is affixed to a particular smart sensor; etc.

As described in block 808, a baseline composite vibration pattern is established from readings generated by multiple smart sensors that are affixed to the multiple intermodal shipping containers, as described in FIG. 7. As described above, this baseline can be taken as the ship is underway, such as while all operational conditions are within predefined nominal ranges. That is, these predefined nominal ranges describe a level of vibration of the deck that is normal when the structural integrity of the cargo ship is intact, the arrangement and securement (i.e., by tie-downs) of the intermodal shipping containers are according to a predefined protocol, gauges/sensors on the drive train indicate that the drive train is operating within normal engine/screw/shaft/bearing parameters, etc. In one embodiment, the baseline composite vibration pattern is re-established (by taking new readings from the multiple smart sensors) in response to a particular event or condition, such as changes to local weather conditions (i.e., rain, snow, sleet, high or low atmospheric temperature, etc.) being experienced by the cargo ship reaching a pre-determined level; new loading/unloading of intermodal shipping containers; entering an area of water known to have different currents/temperatures/etc.; fuel being consumed, thus changing the weight of the cargo ship; etc.

As described in block 810, subsequent readings are then taken from multiple smart sensors on the intermodal shipping containers in order to generate a new composite vibration pattern (also described above in FIG. 7). As described in query block 812, if the new composite vibration pattern is different (i.e., differs beyond some predefined range) from the baseline composite vibration pattern, then the new composite vibration pattern is matched with a known composite vibration pattern in order to identify a cause of the new composite vibration pattern (block 814). In one embodiment, matching the new composite vibration pattern with the known composite vibration pattern identifies/indicates a physical shifting of the multiple intermodal shipping containers. In one embodiment, matching the new composite vibration pattern with the known composite vibration pattern identifies/indicates damage to a non-mechanical physical structure (e.g., the ship's hull, internal structural beams, etc.) of the cargo ship. In one embodiment, matching the new composite vibration pattern with the known composite vibration pattern identifies/indicates damage to a drive train of the cargo ship.

As noted above, the sensor in the smart sensor that is affixed to an intermodal shipping container may include an acoustic sensor (which measures sound that travels through air and/or solids such as structural members of the ship, intermodal shipping containers, etc.). If so, then a processor can incorporate acoustic readings from these acoustic sensors in order to modify the baseline composite vibration pattern, thus creating a baseline vibration/acoustic composite pattern. This baseline vibration/acoustic composite pattern modifies the original baseline composite vibration pattern with the additional sound/sonic information provided by the acoustic sensors, in order to provide additional specificity to a pattern's appearance (i.e., its shape) when a particular cause/event is occurring. The processor then incorporates subsequent acoustic readings from the acoustic sensors in order to generate a new vibration/acoustic composite pattern. In response to the new vibration/acoustic composite pattern being different from the baseline vibration/acoustic composite pattern, the processor matches the new vibration/acoustic composite pattern with a known vibration/acoustic pattern in order to identify a cause of the new vibration/acoustic composite pattern, which may or may not be the same cause as that of the non-acoustic known composite vibration pattern.

Similarly, the sensor in the smart sensor that is affixed to an intermodal shipping container may a chemical sensor that detects a presence of chemicals inside and/or outside that intermodal shipping container. If so, then a processor can incorporate chemical readings from these chemical sensors in the smart sensors in order to modify the baseline composite vibration pattern, thus creating a baseline vibration/chemical composite pattern. This baseline vibration/chemical composite pattern modifies the original baseline composite vibration pattern with the additional chemical information provided by the chemical sensors, in order to provide additional specificity to a pattern's appearance (i.e., its shape) when a particular cause/event is occurring. The processor then incorporates subsequent chemical readings from the chemical sensors in order to generate a new vibration/chemical composite pattern. In response to the new vibration/chemical composite pattern being different from the baseline vibration/chemical composite pattern, the processor matches the new vibration/chemical composite pattern with a known vibration/chemical pattern in order to identify a cause of the new vibration/chemical composite pattern, which may or may not be the same cause as that of the non-chemical known composite vibration pattern. Note that an increase/decrease in chemical levels will impact the sensitivity of the vibration sensor, due to contacts erosion, accelerometer decay, etc., thus leading to the adjusted vibration pattern. Note further that if the chemical level increase is detected by an internal chemical sensor, then an alert can be sounded as to the presence of potentially dangerous chemicals having been released within the intermodal shipping container, leading to emergency procedures (e.g., clean-up, containment, etc.) being implemented.

In one embodiment, the smart sensor is affixed to an interior of an intermodal shipping container, and the sensor in the smart sensor includes (or is) a humidity sensor. In this embodiment, the door to the intermodal shipping container is sealed (e.g., by a door/frame barrier strip) such that humidity, insects, etc. are unable to enter the interior of the intermodal shipping container. Assume that the humidity outside of the intermodal shipping container increases during the ocean voyage of the cargo ship (due to sea spray, etc.). Thus, if there is a breach in the integrity of seal around the door of the intermodal shipping container, then the humidity sensor will detect a rise in the interior humidity level. This information is then used to prompt a crew member to reseal the container, such that the contents are not damaged by the increased interior humidity level.

As noted above, each of the smart sensors may include a uniquely-identified radio frequency identifier (RFID) device. If so, this enables a processor to map a location of each of the multiple intermodal shipping containers by interrogating RFID devices in the smart sensors. This mapping can be done by triangulating the signals coming from the RFID devices, or it may be performed by simply knowing the loading order and position placement of the intermodal shipping containers as they are being loaded onto the cargo ship. By knowing the exact location of each of the intermodal shipping contains, then the processor is able to adjust the baseline composite vibration pattern and the new composite vibration pattern according to the location of each of the multiple intermodal shipping containers such that the new/known patterns are further refined according to the location and environment of the sensors as they take their vibration and other readings. Note further that the RFID-tag information can be further used to fine-tune the vibration patterns, since different weights/materials/etc. in the intermodal shipping container will affect the readings of the vibration sensor.

If a decision has been made to quit monitoring for new patterns (query block 816), such as at the end of an ocean voyage of the cargo ship, then the process ends at terminator block 818. Otherwise, the smart sensors are further monitored in order to generate additional new composite vibration patterns for matching to the same or other known composite vibration patterns (blocks 810-814).

As described herein, smart sensors are affixed to intermodal shipping containers that are loaded onto a cargo ship. An initial baseline of the vibration frequencies and amplitudes from the smart sensors is established once the ship is under way. A significant shift in these frequencies/amplitudes can identify 1) a shift in the cargo, 2) damage to the ship's structure, 3) mechanical (e.g., drive train) problems, etc. Thus, the present invention presents a novel and significant improvement to monitoring cargo ship operational conditions by providing a dynamic sensor grid without having to retrofit the cargo ship.

Note that while the present invention has been described in the context of monitoring conditions of a cargo ship that is under way, the process/system described herein is also useful in monitoring activities/conditions while the intermodal shipping containers are on land. That is, by monitoring accelerometer, chemical, humidity, acoustic, etc. sensors that are affixed to the intermodal shipping containers while on a dock, the history/condition of each intermodal shipping container can also be tracked. For example, if a particular intermodal shipping container had been subject to a severe (beyond a predetermined level) impact, this impact is recorded (either at the intermodal shipping container or by a remote system that interrogates the smart sensor), in order to determine if and/or when any damage to the contents of that intermodal shipping container occurred, whether remedial steps need to be taken to repair the intermodal shipping container and/or its contents, etc.

Note further that monitoring the level of vibrations using an accelerometer-based sensor in the smart sensor enables the detection of a loose intermodal shipping container. That is, if a particular intermodal shipping container is struck by another intermodal shipping container, it is likely that one or both of the intermodal shipping containers have become free of their restraints. Left unresolved (i.e., failing to resecure the restraints), the contents of one or both of the intermodal shipping containers will be damaged, and one or both of the intermodal shipping containers may fall overboard (assuming that they are on the deck of the cargo ship). Thus, the receiving computer, upon detecting such a sudden acceleration (i.e., a first and second order approximation that is indicative of a strong impact), will issue an alert that one or more of the intermodal shipping containers are unsecured, such that appropriate corrective steps are taken.

As noted above, the system described herein allows a computer to monitor the condition of not only the cargo (i.e., the intermodal shipping containers), but the cargo ship itself. As such, the real-time conditions of the cargo ship (as determined by the smart sensor array) are stored, in order to generate a trend pattern of the structural/mechanical condition of the cargo ship. This information is then used to generate a preventative maintenance plan, a retrofitting schedule, and/or a plan to decommission the cargo ship (if conditions decay to the point that repairs/retrofits are not economically feasible).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer-implemented method of monitoring operational conditions of a cargo ship, the method comprising:
    a processor establishing a baseline composite vibration pattern from readings generated by multiple smart sensors, wherein each smart sensor, of the multiple smart sensors, is a uniquely-identified smart sensor that has been affixed to one of multiple intermodal shipping containers, wherein each smart sensor comprises a vibration sensor for detecting mechanical vibration, wherein the multiple intermodal shipping containers have been loaded onto a cargo ship, and wherein the baseline composite vibration pattern is generated by combining two or more frequency plus amplitude vibration patterns generated by two or more of the multiple smart sensors that are affixed to the multiple intermodal shipping containers;
    the processor taking subsequent readings from the multiple smart sensors to generate a new composite vibration pattern, wherein the new composite vibration pattern is generated by combining two or more new frequency plus amplitude vibration patterns generated by two or more of the multiple smart sensors that are affixed to the multiple intermodal shipping containers; and
    the processor, in response to the new composite vibration pattern being different, beyond a predefined range, from the baseline composite vibration pattern, matching the new composite vibration pattern with a known composite vibration pattern in order to identify a cause of the new composite vibration pattern.

2. The computer-implemented method of claim 1, further comprising:
    the processor identifying a physical shifting of the multiple intermodal shipping containers by matching the new composite vibration pattern with the known composite vibration pattern.

3. The computer-implemented method of claim 1, further comprising:
    the processor identifying damage to a non-mechanical physical structure of the cargo ship by matching the new composite vibration pattern with the known composite vibration pattern.

4. The computer-implemented method of claim 1, further comprising:
    the processor identifying damage to a drive train of the cargo ship by matching the new composite vibration pattern with the known composite vibration pattern.

5. The computer-implemented method of claim 1, wherein said each smart sensor further comprises an acoustic sensor, and wherein the method further comprises:
    the processor incorporating acoustic readings from acoustic sensors in the multiple smart sensors to modify the baseline composite vibration pattern to create a baseline vibration/acoustic composite pattern;
    the processor incorporating subsequent acoustic readings from the acoustic sensors to generate a new composite vibration/acoustic pattern; and
    the processor, in response to the new composite vibration/acoustic pattern being different from the baseline composite vibration/acoustic pattern, matching the new composite vibration/acoustic pattern with a known composite vibration/acoustic pattern in order to identify a cause of the new composite vibration/acoustic pattern.

6. The computer-implemented method of claim 1, wherein said each smart sensor further comprises a chemical sensor, and wherein the method further comprises:
    the processor incorporating chemical readings from chemical sensors in the multiple smart sensors to modify the baseline composite vibration pattern to create a baseline composite vibration/chemical pattern;
    the processor incorporating subsequent chemical readings from the chemical sensors to generate a new composite vibration/chemical pattern; and
    the processor, in response to the new composite vibration/chemical pattern being different from the baseline composite vibration/chemical pattern, matching the new composite vibration/chemical pattern with a known composite vibration/chemical pattern in order to identify a cause of the new composite vibration/chemical pattern.

7. The computer-implemented method of claim 1, further comprising:
    in response to a pre-determined level of change in weather conditions currently being experienced by the cargo ship, the processor re-establishing the baseline composite vibration pattern by taking new readings from the multiple smart sensors.

8. The computer-implemented method of claim 1, wherein each of the smart sensors comprises a uniquely-identified radio frequency identifier (RFID) device, and wherein the computer implemented method further comprises:
    the processor mapping a location of each of the multiple intermodal shipping containers by interrogating RFID devices in the multiple smart sensors; and
    the processor adjusting the baseline composite vibration pattern and the new composite vibration pattern according to the location of each of the multiple intermodal shipping containers.

9. A non-transitory computer readable storage medium containing computer executable instructions to perform a method for monitoring operational conditions of a cargo ship, the method comprising:
    establishing a baseline composite vibration pattern from readings generated by multiple smart sensors, wherein each smart sensor, of the multiple smart sensors, is a uniquely-identified smart sensor that has been affixed to one of multiple intermodal shipping containers, wherein each smart sensor comprises a vibration sensor for detecting mechanical vibration, and wherein the multiple intermodal shipping containers have been loaded onto a cargo ship, and wherein the baseline composite vibration pattern is generated by combining two or more frequency plus amplitude vibration patterns generated by two or more of the multiple smart sensors that are affixed to the multiple intermodal shipping containers;

taking subsequent readings from the multiple smart sensors to generate a new composite vibration pattern, wherein the new composite vibration pattern is generated by combining two or more new frequency plus amplitude vibration patterns generated by two or more of the multiple smart sensors that are affixed to the multiple intermodal shipping containers; and in response to the new composite vibration pattern being different from the baseline composite vibration pattern, matching the new composite vibration pattern with a known composite vibration pattern in order to identify a cause of the new composite vibration pattern.

10. The non-transitory computer readable storage medium of claim 9, wherein the method further comprises:

identifying a physical shifting of the multiple intermodal shipping containers by matching the new composite vibration pattern with the known composite vibration pattern.

11. The non-transitory computer readable storage medium of claim 9, wherein the method further comprises:

identifying damage to a non-mechanical physical structure of the cargo ship by matching the new composite vibration pattern with the known composite vibration pattern.

12. The non-transitory computer readable storage medium of claim 9, wherein the method further comprises:

identifying damage to a drive train of the cargo ship by matching the new composite vibration pattern with the known composite vibration pattern.

13. The non-transitory computer readable storage medium of claim 9, wherein said each smart sensor further comprises an acoustic sensor, and wherein the method further comprises:

incorporating acoustic readings from acoustic sensors in the multiple smart sensors to modify the baseline composite vibration pattern to create a baseline composite vibration/acoustic pattern;

incorporating subsequent acoustic readings from the acoustic sensors to generate a new composite vibration/acoustic pattern; and in response to the new composite vibration/acoustic pattern being different from the baseline composite vibration/acoustic pattern, matching the new composite vibration/acoustic pattern with a known composite vibration/acoustic pattern in order to identify a cause of the new composite vibration/acoustic pattern.

14. The non-transitory computer readable storage medium of claim 9, wherein said each smart sensor further comprises a chemical sensor, and wherein the method further comprises:

incorporating chemical readings from chemical sensors in the smart sensors to modify the baseline composite vibration pattern to create a baseline composite vibration/chemical pattern;

incorporating subsequent chemical readings from the chemical sensors to generate a new composite vibration/chemical pattern; and in response to the new composite vibration/chemical pattern being different from the baseline composite vibration/chemical pattern, matching the new composite vibration/chemical pattern with a known composite vibration/chemical pattern in order to identify a cause of the new composite vibration/chemical pattern.

15. The non-transitory computer readable storage medium of claim 9, wherein the method further comprises:

in response to a pre-determined level of change in weather conditions currently being experienced by the cargo ship, re-establishing the baseline composite vibration pattern by taking new readings from the multiple smart sensors.

16. The non-transitory computer readable storage medium of claim 9, wherein each of the smart sensors comprises a uniquely-identified radio frequency identifier (RFID) device, and wherein the method further comprises:

mapping a location of each of the multiple intermodal shipping containers by interrogating RFID devices in the multiple smart sensors; and adjusting the baseline composite vibration pattern and the new composite vibration pattern according to the location of each of the multiple intermodal shipping containers.

17. A system comprising:

a processor, a computer readable memory, and a computer readable storage media;

first program instructions to establish a baseline composite vibration pattern from readings generated by multiple smart sensors, wherein each smart sensor, of the multiple smart sensors, is a uniquely-identified smart sensor that has been affixed to one of multiple intermodal shipping containers, wherein each smart sensor comprises a vibration sensor for detecting mechanical vibration, and wherein the multiple intermodal shipping containers have been loaded onto a cargo ship, and wherein the baseline composite vibration pattern is generated by combining two or more frequency plus amplitude vibration patterns generated by two or more of the multiple smart sensors that are affixed to the multiple intermodal shipping containers;

second program instructions to take subsequent readings from the multiple smart sensors to generate a new composite vibration pattern, wherein the new composite vibration pattern is generated by combining two or more new frequency plus amplitude vibration patterns generated by two or more of the multiple smart sensors that are affixed to the multiple intermodal shipping containers; and third program instructions to, in response to the new composite vibration pattern being different from the baseline composite vibration pattern, match the new composite vibration pattern with a known composite vibration pattern in order to identify a cause of the new composite vibration pattern; and wherein the first, second, and third program instructions are stored on the computer readable storage media for execution by the processor via the computer readable memory.

18. The system of claim 17, further comprising:

fourth program instructions to identify a physical shifting of the multiple intermodal shipping containers by matching the new composite vibration pattern with the known composite vibration pattern; and wherein the fourth program instructions are stored on the computer readable storage media for execution by the processor via the computer readable memory.

19. The system of claim 17, further comprising:

fourth program instructions to, in response to a pre-determined level of change in weather conditions currently being experienced by the cargo ship, re-establish the baseline composite vibration pattern by taking new readings from the multiple smart sensors; and wherein the fourth program instructions are stored on the computer readable storage media for execution by the processor via the computer readable memory.

20. The system of claim 17, wherein each of the smart sensors comprises a uniquely-identified radio frequency identifier (RFID) device, and wherein the system further comprises:
- fourth program instructions to map a location of each of the multiple intermodal shipping containers by interrogating RFID devices in the multiple smart sensors; and
- fifth program instructions to adjust the baseline composite vibration pattern and the new composite vibration pattern according to the location of each of the multiple intermodal shipping containers; and wherein
- the fourth and fifth program instructions are stored on the computer readable storage media for execution by the processor via the computer readable memory.

* * * * *